US005860987A

United States Patent [19]
Ratcliff et al.

[11] Patent Number: 5,860,987
[45] Date of Patent: Jan. 19, 1999

[54] SURGICAL RETRACTOR

[75] Inventors: Keith Ratcliff, Sandy Hook; Keith L. Milliman, Bethel; Henry R. Sienkiewicz, Stamford, all of Conn.

[73] Assignee: United States Surgical Corporation, Norwalk, Conn.

[21] Appl. No.: 762,514

[22] Filed: Dec. 10, 1996

Related U.S. Application Data

[63] Continuation of Ser. No. 329,007, Oct. 4, 1994, abandoned.

[51] Int. Cl.$^6$ ............................................. A61B 17/24
[52] U.S. Cl. ................................... 606/113; 606/110
[58] Field of Search ............................. 606/106, 110, 606/113, 114, 127, 108

[56] References Cited

U.S. PATENT DOCUMENTS

| 480,870 | 8/1892 | Harris . |
| 668,647 | 2/1901 | Jaenicke . |
| 1,461,864 | 7/1923 | Day . |
| 1,470,914 | 10/1923 | Day . |
| 2,054,149 | 9/1936 | Wappler . |
| 3,181,533 | 5/1965 | Heath . |
| 3,828,790 | 8/1974 | Curtiss et al. . |
| 3,903,892 | 9/1975 | Komiya . |
| 4,592,355 | 6/1986 | Antebi . |
| 4,718,419 | 1/1988 | Okada . |
| 4,744,363 | 5/1988 | Hasson . |
| 4,909,789 | 3/1990 | Taguchi et al. . |
| 5,084,054 | 1/1992 | Bencini et al. . |
| 5,108,406 | 4/1992 | Lee . |
| 5,113,846 | 5/1992 | Hiltebrandt et al. . |
| 5,116,357 | 5/1992 | Eberbach . |
| 5,122,147 | 6/1992 | Sewell, Jr. . |
| 5,123,906 | 6/1992 | Kelman . |
| 5,163,942 | 11/1992 | Rydell . |
| 5,171,233 | 12/1992 | Amplatz et al. . |
| 5,171,314 | 12/1992 | Dulebohn . |
| 5,190,554 | 3/1993 | Coddington, III et al. . |
| 5,196,022 | 3/1993 | Bilweis . |
| 5,201,741 | 4/1993 | Dulebohn . |
| 5,207,686 | 5/1993 | Dolgin . |
| 5,234,439 | 8/1993 | Wilk et al. . |
| 5,281,238 | 1/1994 | Chin et al. . |
| 5,290,294 | 3/1994 | Cox et al. . |
| 5,330,482 | 7/1994 | Gibbs . |
| 5,383,882 | 1/1995 | Buess et al. . |
| 5,417,684 | 5/1995 | Jackson et al. . |

FOREIGN PATENT DOCUMENTS

| 0499243 | 8/1992 | European Pat. Off. . |
| 0611561 | 8/1994 | European Pat. Off. . |
| 3804849 | 9/1988 | Germany . |
| 9102493 | 3/1991 | WIPO . |

OTHER PUBLICATIONS

Hennig et al., "Endoscopic Removal of Foreign Bodies Using a Newly Developed Extractor", Endoscopy, 20 (1988) pp. 70–72.

Ponsky et al., "A Simple Method of Infundibular Retraction During Laparoscopic Cholecystectomy", Surgical Endoscopy (1991) 5:57–58.

Primary Examiner—Michael A. Brown
Assistant Examiner—Benjamin K. Koo

[57] ABSTRACT

A surgical retractor device for manipulating organs during an endoscopic or laparoscopic surgical procedure. The retractor device includes a loop of material at a distal end of the instrument which is extendable and retractable from the elongated body portion of the instrument. The loop of material may be detached to be wrapped about an organ and reattached to secure the organ. Once the organ is secured, the loop of material may be retracted into the body portion of the instrument to manipulate the organ.

13 Claims, 10 Drawing Sheets

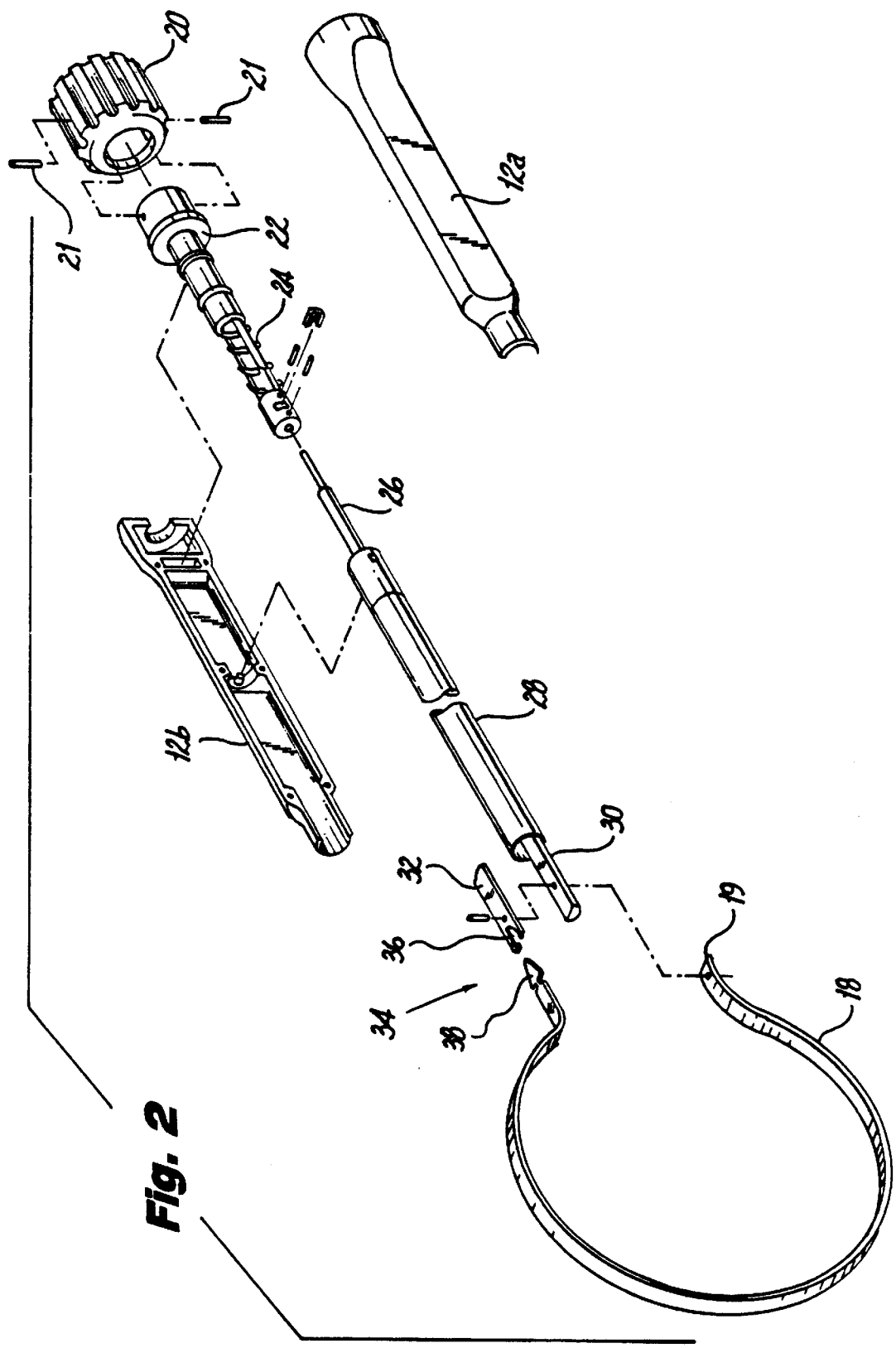

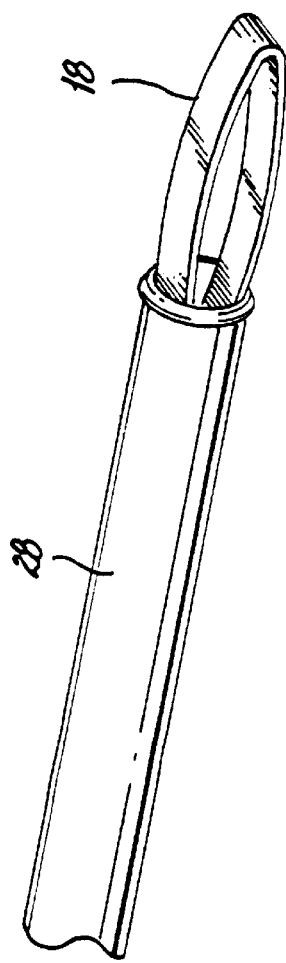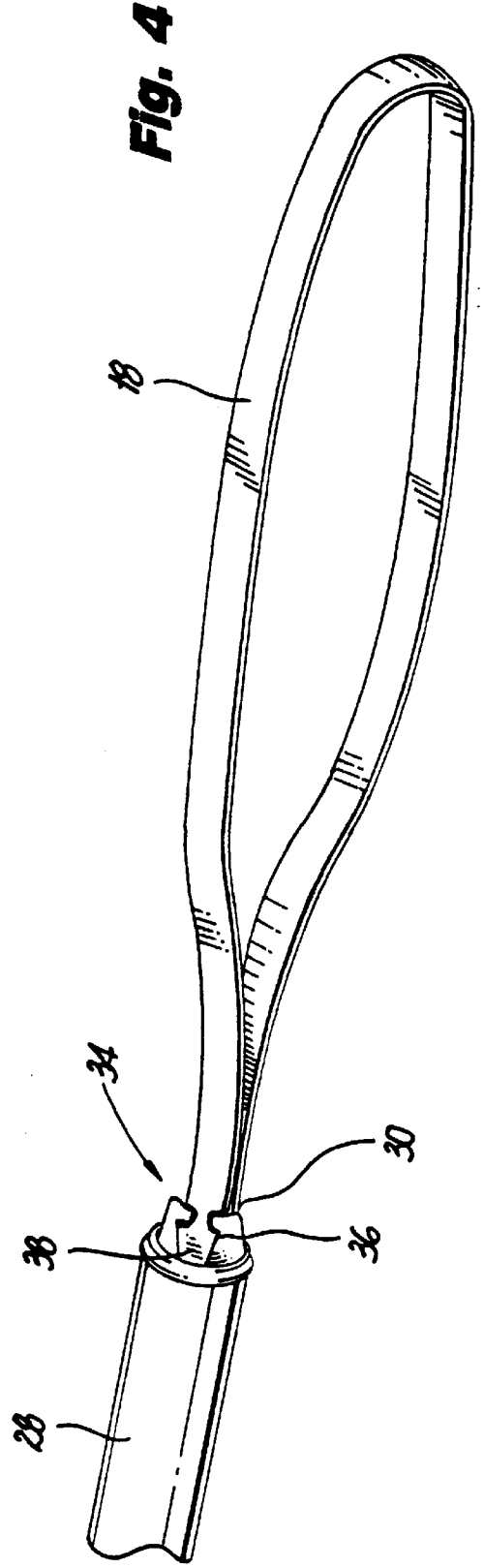

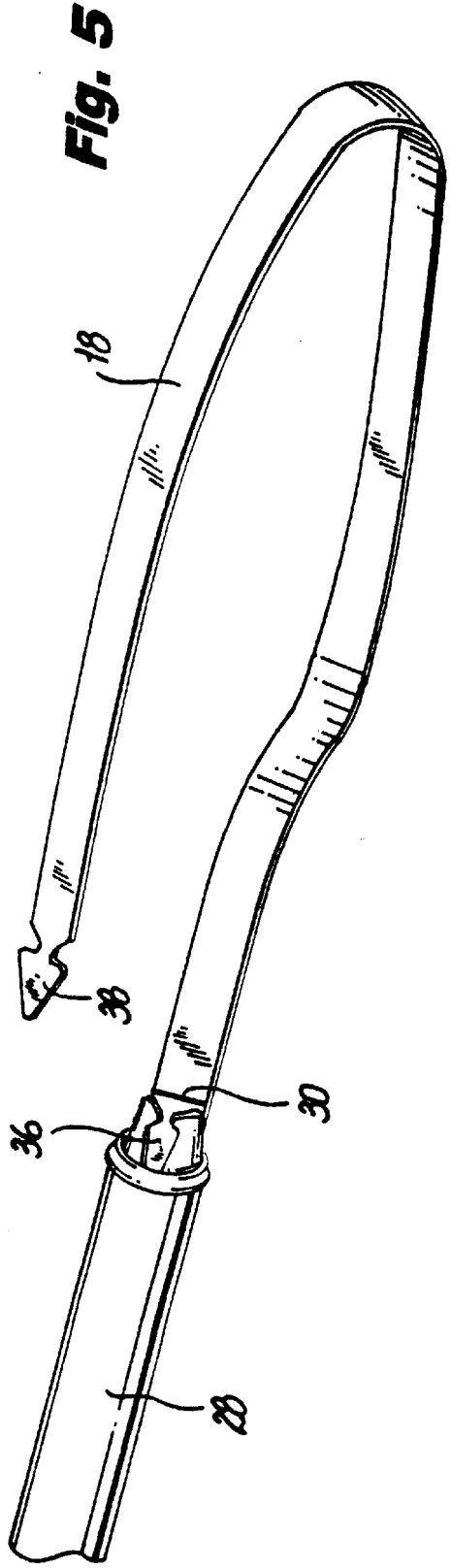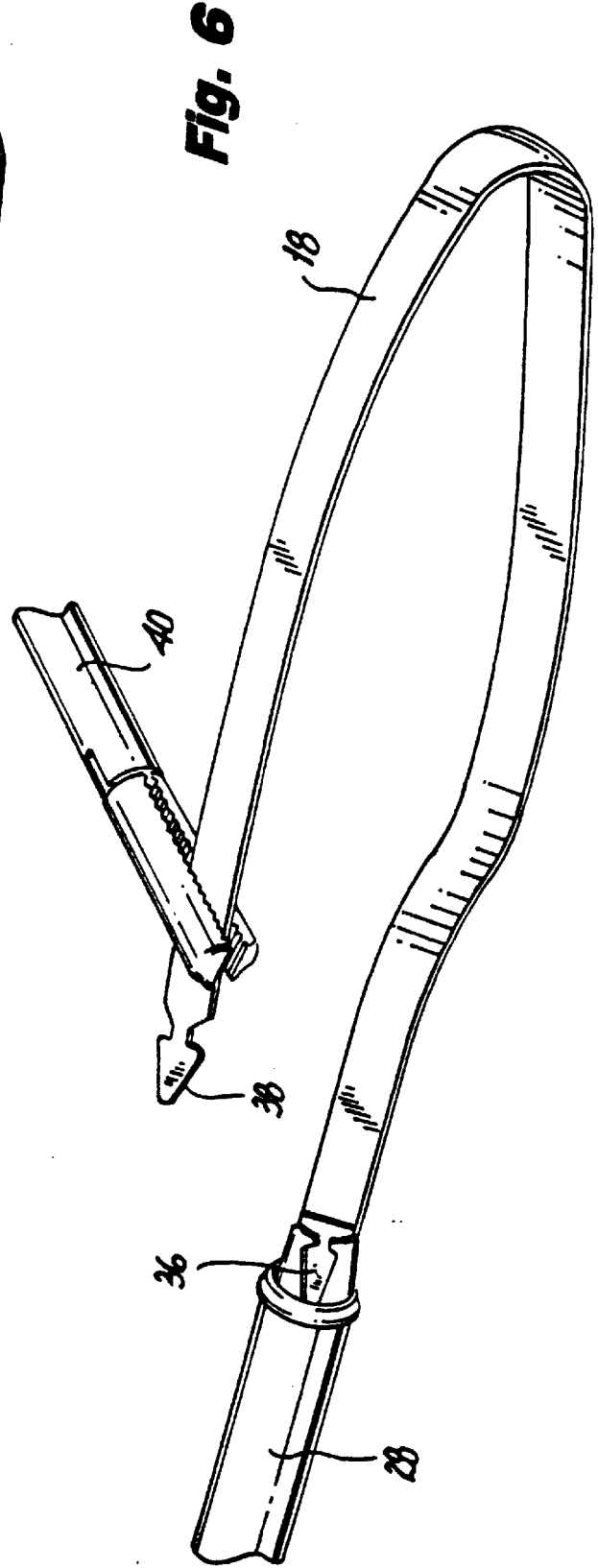

SURGICAL RETRACTOR

This is a continuation of U.S. application Ser. No. 08/329,007, filed on Oct. 4, 1994 abandoned.

BACKGROUND OF THE INVENTION

1. Field of the Invention

This application relates to surgical instruments and, more particularly, to a surgical retractor which includes a grasping mechanism formed as a loop which may be wrapped around tissue or organs for manipulating the tissue or organ during an endoscopic surgical procedure.

2. Discussion of the Prior Art

In endoscopic and laparoscopic surgical procedures, it is often necessary to provide instrumentation to move or manipulate tissue and organs in the area of operation. Generally, laparoscopic surgical procedures involve the introduction of carbon dioxide to insufflate a body cavity, e.g., the abdomen, to provide a working area for the surgeon. After the abdomen is insufflated, a trocar device is utilized to puncture the peritoneum to provide an access port through the abdominal wall for the introduction of surgical instrumentation. Generally, a trocar cannula is placed through the abdominal wall for each piece of surgical instrumentation which is necessary to carry out the surgical procedure. In this manner, the surgeon may view the surgical site through an endoscope provided through a first trocar cannula, and utilize a second trocar cannula to introduce a surgical instrument such as a grasper, scissors, clip appliers, stapler, and any other surgical instrument which may be necessary during that particular surgical procedure.

Although the insufflation gas expands the abdomen to permit the surgeon to view the surgical site, it is often necessary to manipulate the internal organs or tissues to provide a clear path to the surgical objective. In the prior art, it has been known to utilize grasping tools which pull on the organs or tissues to move them out of the way to provide a clear visual path for the surgeon. However, these devices may damage the organs or tissues which they grasp, and consequently these devices are utilized only when absolutely necessary. In order to avoid the problems associated with grasping tools, endoscopic retractor mechanisms have been developed which are utilized to push and hold the tissue or organs away from the surgical site. Typically, these devices include paddles and/or fingers which expand after the retractor has been inserted into the abdomen through the trocar cannula. Such devices are disclosed in, for example, U.S. Pat. No. 4,654,028 to Suma, U.S. Pat. No. 4,909,789 to Taguchi et al., and U.S. Pat. No. 5,195,505 to Josefsen. Other retractor devices include collapsible fingers joined by webs of resilient material which expand to form the retractor. These devices are disclosed in, for example, U.S. Pat. No. 4,190,042 to Sinnreich and U.S. Pat. No. 4,744,363 to Hasson. Other devices include retractors having expandable frames for supporting expandable latex sheaths or covers, such as that described in U.S. Pat. No. 5,178,133 to Pena.

While one or more of the aforementioned devices has been successfully used in laparoscopic procedures, larger organs, such as the intestine and/or stomach, tend to be too large and too heavy to be properly supported by these retractors. Consequently, the retractors have difficulty in clearing the surgical field to provide access for the surgeon to the surgical site. Due to the small size of the instrumentation, particularly the trocar cannula through which these instruments must pass, it is difficult to provide a retractor mechanism which can support or otherwise manipulate large and pliable organs such as the intestines or stomach.

Therefore, a need exists for a retractor mechanism which may be utilized to manipulate large organs without damaging the tissue of these organs, and which is reliable as far as the strength and durability of the instrument is concerned. A need also exists for a retractor instrument which may clear the surgical site of heavy organs and tissue, where the instrument is small in relation to the organ and may be utilized with conventional trocar cannulas to provide access to the site during an endoscopic or laparoscopic surgical procedure.

The device disclosed herein overcomes the disadvantages associated with the prior art and provides a lightweight retractor device which allows the surgeon to manipulate large organs and other pliable tissue.

SUMMARY OF THE INVENTION

A novel surgical retractor disclosed herein obviates the disadvantages encountered in the prior art and provides a retractor mechanism for grasping and holding organs and tissues at the surgical site. The instrument includes an elongated body portion, an actuator mechanism disposed at a proximal end of the body portion, a loop of material disposed at a distal end of the body portion, the loop of material being extendable and retractable with respect to the body portion in response to the actuator mechanism, and a coupling mechanism for permitting disconnection and reconnection of the loop. Preferably, the actuator mechanism is disposed in a handle member and includes a drive screw mechanism operatively associated with a rotatable knob. The surgeon can turn the rotatable knob to turn a screw housing and move the drive screw within the handle. The body portion of the instrument includes an outer tube member and an inner rod member or elongate member to which the drive screw is connected. The loop of material is preferably associated with the distal end of the inner rod. Therefore, manipulation of the actuator mechanism at the proximal end of the instrument causes movement of the loop of material at the distal end of the instrument.

Alternately, the actuator mechanism can be an elongate member or inner rod that slides longitudinally through a handle member and outer tube. The loop of material is preferably associated with the distal end of the elongate member. The surgeon can push or pull the elongate member to control the deployment of the loop of material The loop of material is preferably a flexible material such as plastic, metallic bands, i.e., steel or shape memory alloy, or a textile material such as surgical mesh, cloth, nylon, etc. The loop of material is preferably detachable from the distal end of the inner rod to permit the loop to be opened and then wrapped around an organ at the surgical site. The loop can then be reconnected and at least partially retracted within the outer tube of the instrument to tighten the loop.

In one embodiment, a connector member is secured to the distal end of the inner rod or elongate member. One end of the loop material is fixedly secured to the inner rod while the other end is detachably secured to the connector member. In another embodiment, the loop material is fixedly secured to the inner rod and a detachable break in the loop material is provided at a position spaced from the inner rod. In this embodiment, a locking sleeve is preferably provided which fits over the connection to prevent inadvertent detachment of the loop of material. Preferably, the loop of material is detachable through the provision of a latch spring associated with the distal end of the instrument and a clip member associated with a free end of the loop. The latch spring and clip member serve to fixedly close the loop of material when the proximal/detachable portion(s) of the loop are withdrawn into the outer tube of the instrument. Alternatively, the loop can be detachable through the provision of a keyway connection such as, for example, a dove-tail connection, which permits easy detachment and reconnection within the abdomen of the patient.

In use, the loop of material is at least partially retracted within the outer tube of the instrument and the instrument is introduced into the abdomen through a trocar cannula. Once inside the patient, the loop is extended out of the outer tube until the loop connection is exposed. The surgeon can then grasp the loop of material near the connection with a grasping tool which is insertable through a second trocar cannula and the loop can be disconnected at the connection. The loop can then be wrapped around the organ, such as the intestine or other pliable organ, and then reconnected to form a closed loop. Once reconnected, the loop of material can then be at least partially retracted into the outer tube of the instrument to either tighten the loop about the organ and/or ensure the loop remains closed. The instrument can then be used to hold the organ away from the surgical site or to advantageously orient the organ while another instrument performs a surgical task thereon. To release the organ, the loop of material is extended until the loop connection is exposed, and then the loop may be disconnected to release the organ.

BRIEF DESCRIPTION OF THE DRAWINGS

The foregoing and other features of the present retractor instrument will become more readily apparent and may be understood by referring to the following detailed description of illustrative embodiments of the retractor, taken in conjunction with the accompanying drawings, in which:

FIG. 2 illustrates a perspective exploded view of the instrument of FIG. 1;

FIG. 3 illustrates a perspective view of the grasping loop mechanism at the distal end of the retractor of FIG. 1 in the retracted position;

FIG. 4 illustrates the grasping loop mechanism of FIG. 3 in the fully extended position;

FIG. 5 illustrates the grasping loop mechanism in a detached condition;

FIG. 6 illustrates a perspective view of the retractor device in use in which the grasping loop mechanism is being manipulated by a surgeon utilizing a separate instrument at the surgical site;

DETAILED DESCRIPTION OF THE PREFERRED EMBODIMENTS

Figure 1:
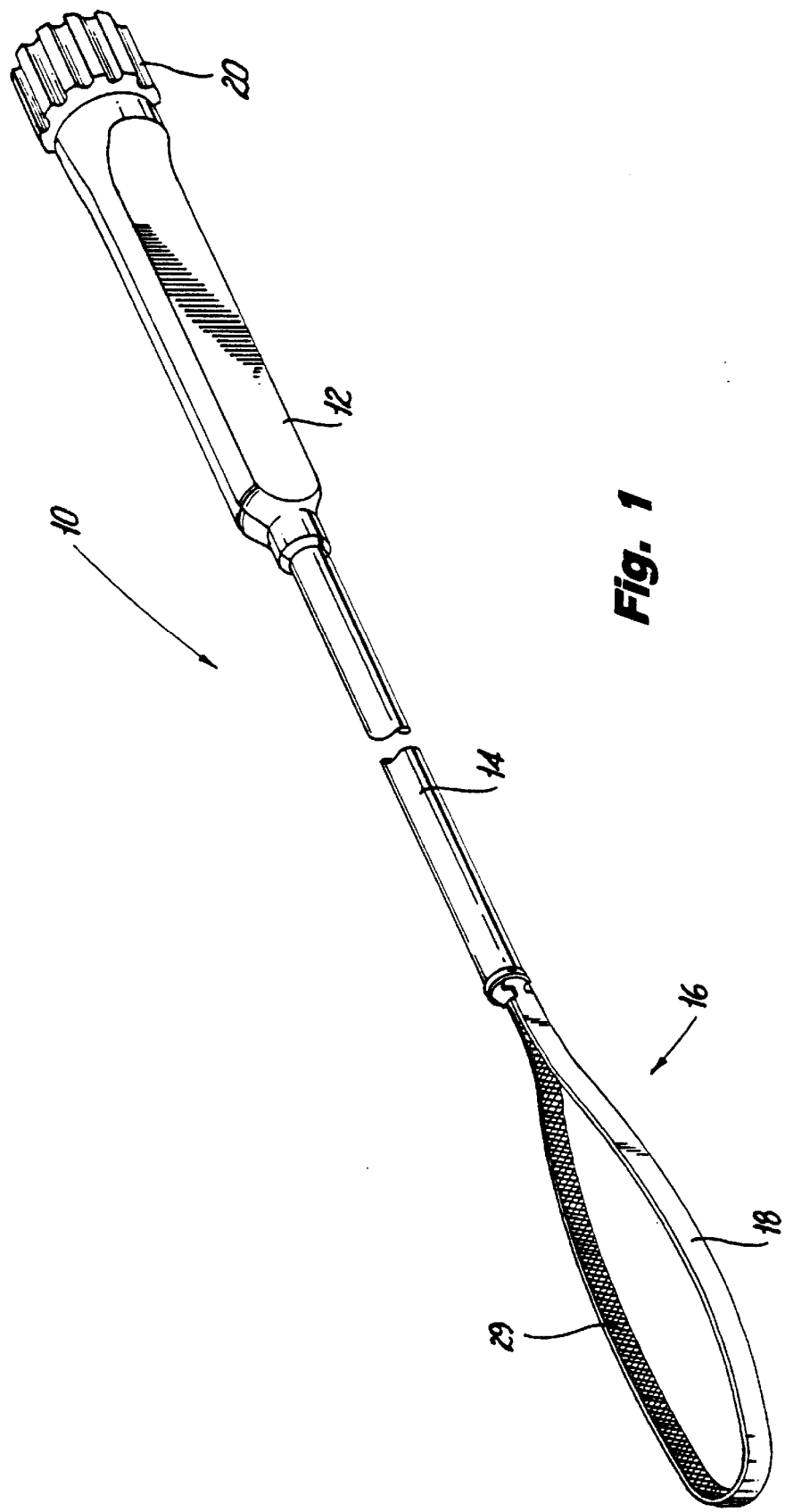
FIG. 1 illustrates a perspective view of a preferred embodiment of a surgical retractor instrument.

Referring now to the drawings, in which like reference numerals identify similar or identical elements throughout the several views, there is illustrated the retractor device 10 in FIG. 1. Retractor device 10 is particularly suited for manipulating organs during an endoscopic or laparoscopic surgical procedure. Retractor device 10 includes a handle 12, an elongated endoscopic body portion 14, and a snare-like grasping mechanism 16 which includes a loop of material 18 whose function will be described below. An actuator knob 20 is also provided for extending and retracting the grasping mechanism 16 with respect to the body portion 14.

As seen in FIG. 2, handle 12 preferably includes handle halves 12a and 12b which enclose an actuator mechanism which includes a drive screw assembly for retracting and extending the grasping mechanism 16. The drive screw assembly includes a screw housing 22 and a drive screw 24. Screw housing 22 is coupled for rotational movement to actuator knob 20, preferably through the provision of pins 21. Screw housing 22 includes internal threads which mate with drive screw 24 to move drive screw 24 distally and proximally with respect to handle 12 upon clockwise and counterclockwise rotation of actuator knob 20.

Drive screw 24 is connected to the proximal end of inner rod member 26. Inner rod 26 and outer tube member 28, form elongated body portion 14. Loop member 18 is connected to the distal end 30 of inner rod member 26 and is movable therewith.

Referring to FIGS. 2 and 5, it is seen that end 19 of loop member 18 is secured to distal end 30 of inner rod member 26 in any suitable manner, such as heat staking, screws, rivets, etc. Also connected to the distal end of inner rod member 26 is loop connector member 32 to which the opposite end of loop member 18 is detachably connected through keyway connector 34. Loop connector member 32 has at its distal end a female dove-tail connection 36 to which male dove-tail connection 38 of loop member 18 is detachably connected. The dove-tail connectors 36 and 38 form keyway connection 34 and permit the attachment and detachment of one end of the loop member 18 to permit loop member 18 to be fit around an organ and then reconnected to manipulate the organ.

Referring now to FIGS. 3–6, the operation of retractor device 10 will now be described. During an endoscopic surgical procedure, after the abdomen of the patient has been insufflated and a trocar cannula has been put in place, retractor device 10 is introduced into the abdomen through the trocar cannula. In order to slide the retractor device 10 through the trocar cannula, actuator knob 20 is rotated along with screw housing 22 to move drive screw 24 in a proximal direction, thus drawing inner rod member 26 and at least a portion of loop member 18 into outer tube member 28 (FIG. 3). Retractor device 10 is then inserted through the trocar cannula and moved into position adjacent the organ to be manipulated. Additional trocar cannulas positioned in the abdomen of the patient provide access for an endoscope for the surgeon to view the surgical site, as well as other instrumentation to perform the surgical procedure.

Once the retractor device is in position a desired position, actuator knob 20 is rotated along with screw housing 22 to advance drive screw 24 distally, which consequently extends inner rod member 26 through outer tube member 28 so that loop member 18 is extended to the position shown in FIG. 4. The surgeon can then insert a grasping tool 40 through one of the other trocar cannulas and grasp loop member 18 as shown in FIG. 6. The surgeon may then disconnect loop member 18 at keyway connection 34, by lifting male dove-tail connector 38 away from female dove-tail connector 36.

Utilizing the grasping instrument 40, the surgeon can then wrap loop member 18 around the organ to be manipulated, and then reconnects loop member 18 at keyway connection 34. Once male dove-tail connector 38 is repositioned within female dove-tail connector 36, in the position shown in FIG. 4, actuator knob 20 is rotated to move drive screw 24 in a proximal direction which draws inner rod member 26 into outer tube member 38. Continued rotation of actuator knob 20 draws loop member 18 into outer tube member 28, thus tightening the loop about the organ. With the organ properly grasped, the surgeon can then manipulate the retractor and organ as desired. The loop can be provided with a textured or irregular inner surface (29 in FIG. 1) to prevent or inhibit slippage of the organ.

Once the surgical procedure is complete, the surgeon reverses the above process, rotating actuator knob 20 to move drive screw 24 in a distal direction, so that loop member 18 extends out of outer tube member 28 to the position shown in FIG. 4 so that the keyway connection 34 can once again be disconnected to release the organ. Once the organ is released, the surgeon can either reconnect the keyway connection 34 and withdraw the loop member 18 into outer tube member 28, or the entire retractor device 10 can be withdrawn through the trocar cannula even with the loop member 18 in the position shown in FIG. 5. This is possible because of the flexibility of the loop member 18, which will merely straighten to a point where it can be withdrawn through the trocar cannula without obstruction.

Figure 7:
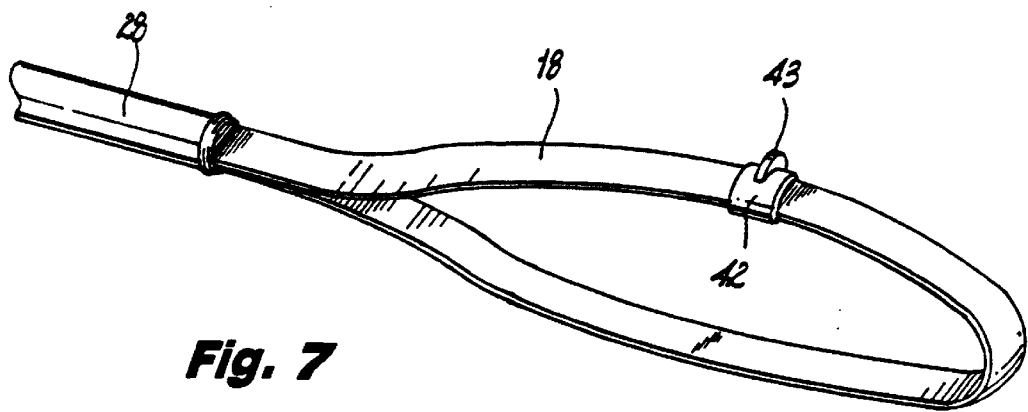
FIG. 7 illustrates another preferred embodiment of the grasping loop mechanism of the retractor device in which the grasping loop mechanism is in the assembled condition.
Figure 8:
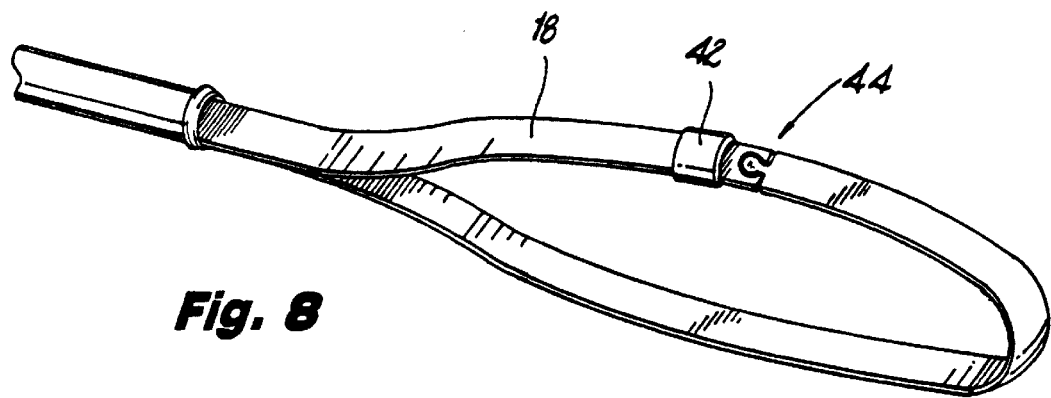
FIG. 8 illustrates a keyway connection of the grasping loop mechanism of the retractor device of FIG. 7.
Figure 9:
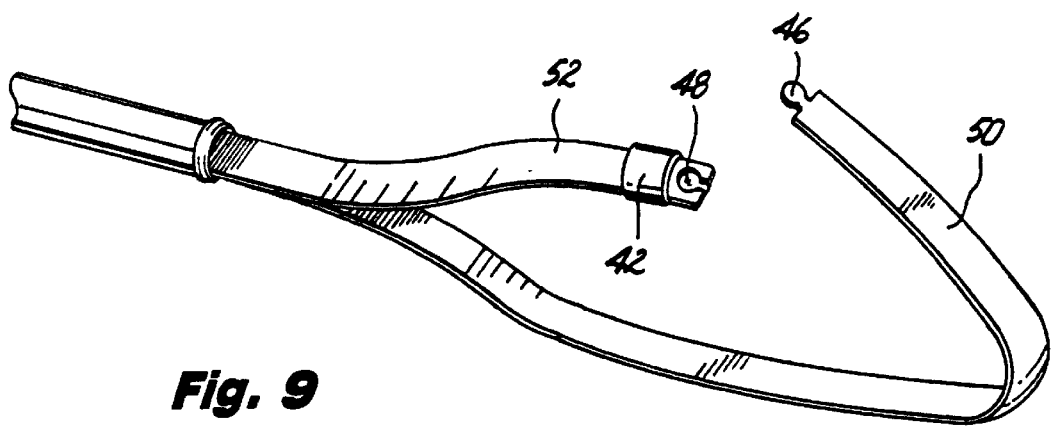
FIG. 9 illustrates the grasping loop mechanism of FIG. 7 in the disassembled condition.

Turning now to FIGS. 7–9, there is illustrated an alternate, preferred embodiment of the retractor device 10 of FIG. 1. In this embodiment, loop member 18 is secured at both ends to the distal end of inner rod member 26. Keyway connection 44 is provided in the loop so that the loop can be disconnected without having to fully extend the loop member 18 out of the outer tube member 28. As seen in FIG. 7, a locking sleeve 42 is provided which is slidably movable over loop member 18 to cover the keyway connection 44. Locking sleeve 42 serves to prevent inadvertent disconnection of the segments 50 and 52 of the loop member 18. Projection 43 (FIG. 7) can be provided on locking sleeve 42 to facilitate grasping and manipulation of the sleeve during use. In use, the surgeon will utilize a grasping tool such as instrument 40 of FIG. 6 to grasp locking sleeve 42 and slide sleeve 42 away from the keyway connection 44. The surgeon can then utilize the instrument 40 to disconnect the keyway and separate male connector 46 from female connector 48 to separate loop member 18 into first segment 50 and second segment 52. After the organ is positioned within the loop, male connector 46 is reconnected with female connector 48 and locking sleeve 42 is slid over the keyway connection 44 to hold the organ within the loop member 18. Actuator knob 20 can then be rotated to draw loop member 18 into outer tube member 28 to secure the organ in loop member 18.

Figure 10:
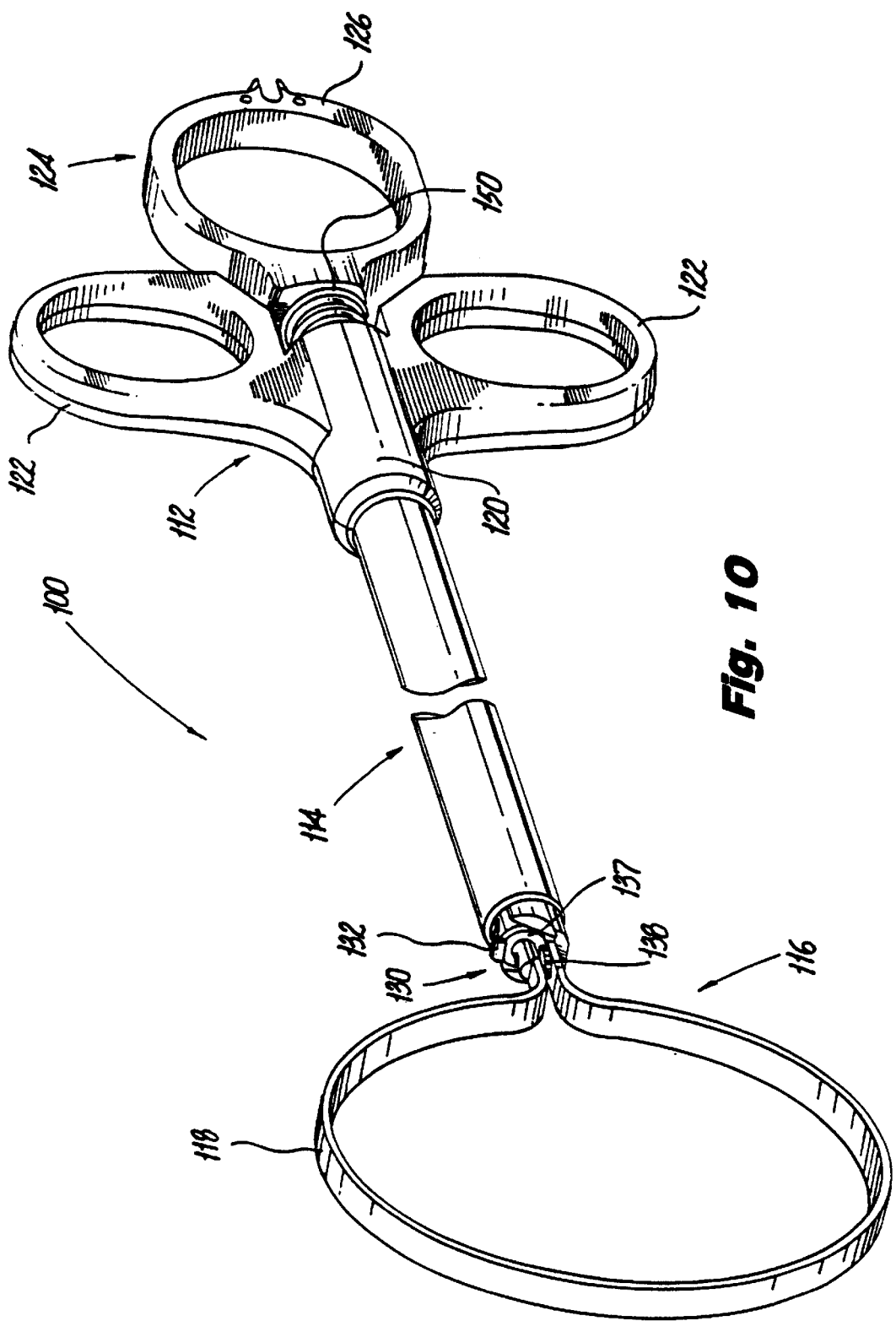
FIG. 10 illustrates another preferred embodiment of a looped grasping instrument.

Yet another preferred embodiment of a retractor device is shown in FIGS. 10–14. In FIG. 10, retractor device 100 includes elongate endoscopic portion 114 extending distally from handle assembly 112. Handle assembly 112 includes tubular body 120 and grasping rings 122. Actuator 124 includes inner rod 128 (FIGS. 11–14) which passes through body 120 and endoscopic portion 114 and has actuator grasping ring 126 disposed at the proximal end thereof. The distal end of instrument 100 has grasping mechanism 116 which includes loop 118. The distal end of inner rod 128 is associated with connector mechanism 130, which reciprocates within endoscopic portion 114 upon movement of actuator 124.

Figure 11:
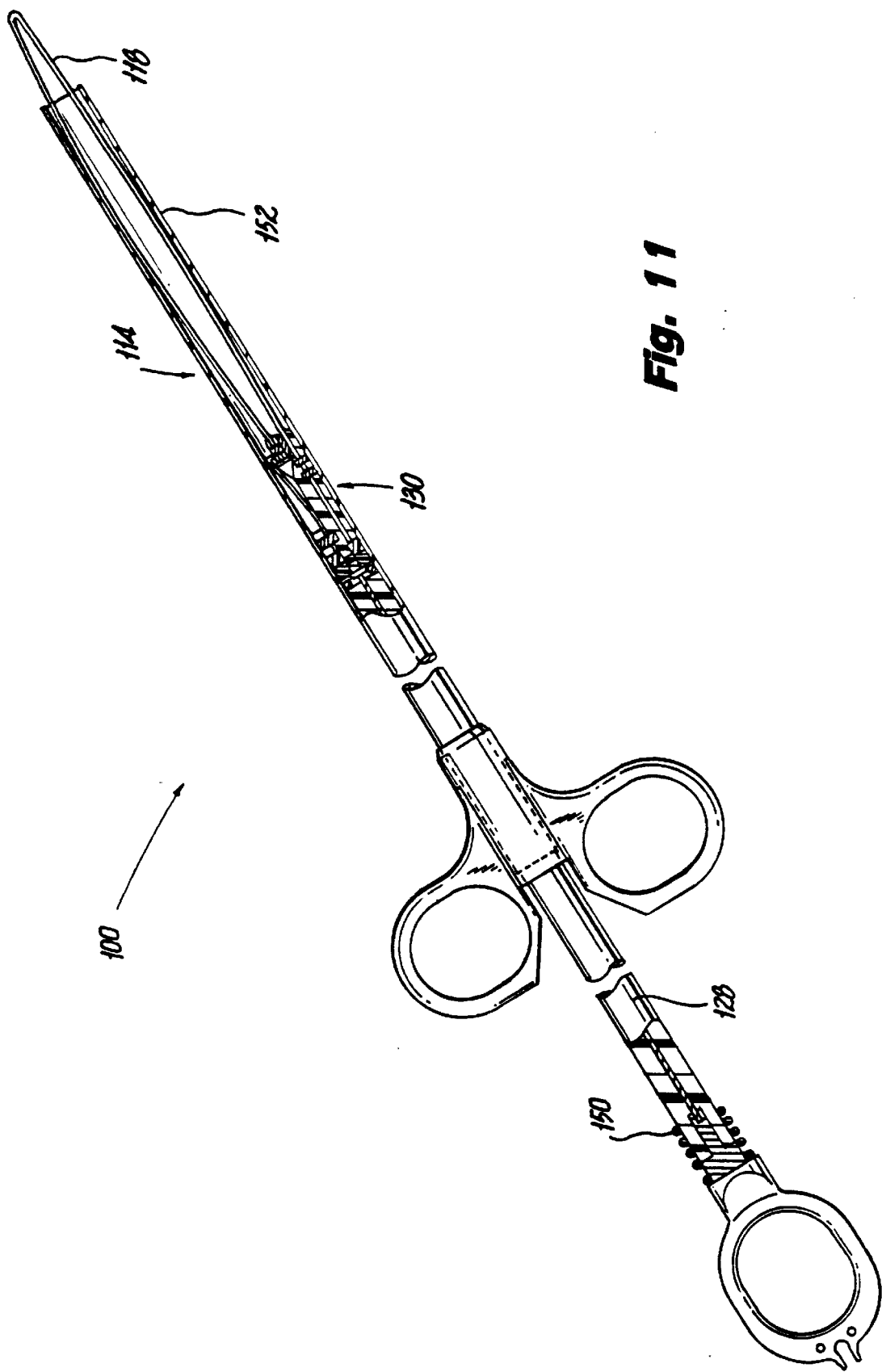
FIG. 11 illustrates the instrument of FIG. 10 with the loop mechanism retracted into an outer tube.

Turning to FIG. 11, the actuation mechanism is shown in a proximal position, wherein inner rod 128 is withdrawn proximally and loop 118 is substantially disposed within outer tube 152 of endoscopic portion 114. In this position, the distal end of the instrument is easily inserted through a cannula to access an operative site.

Figure 12:
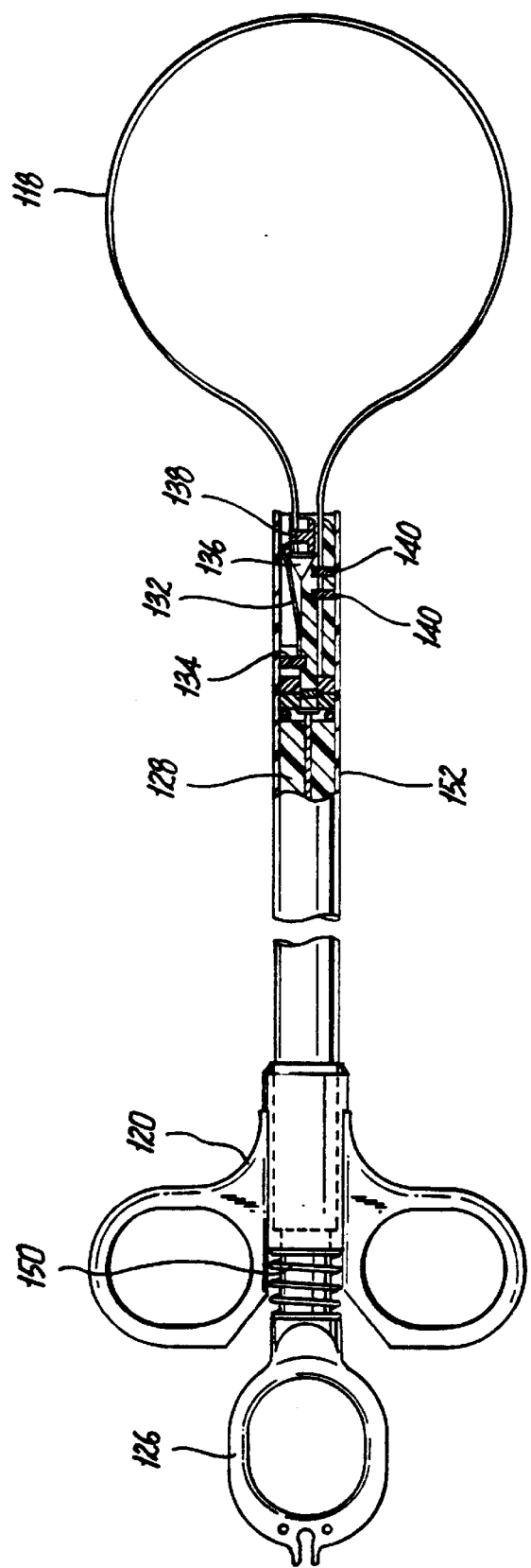
FIGS. 12–14 illustrate a preferred embodiment of the loop detachment mechanism shown on the instrument in FIGS. 10 and 11.
Figure 13:
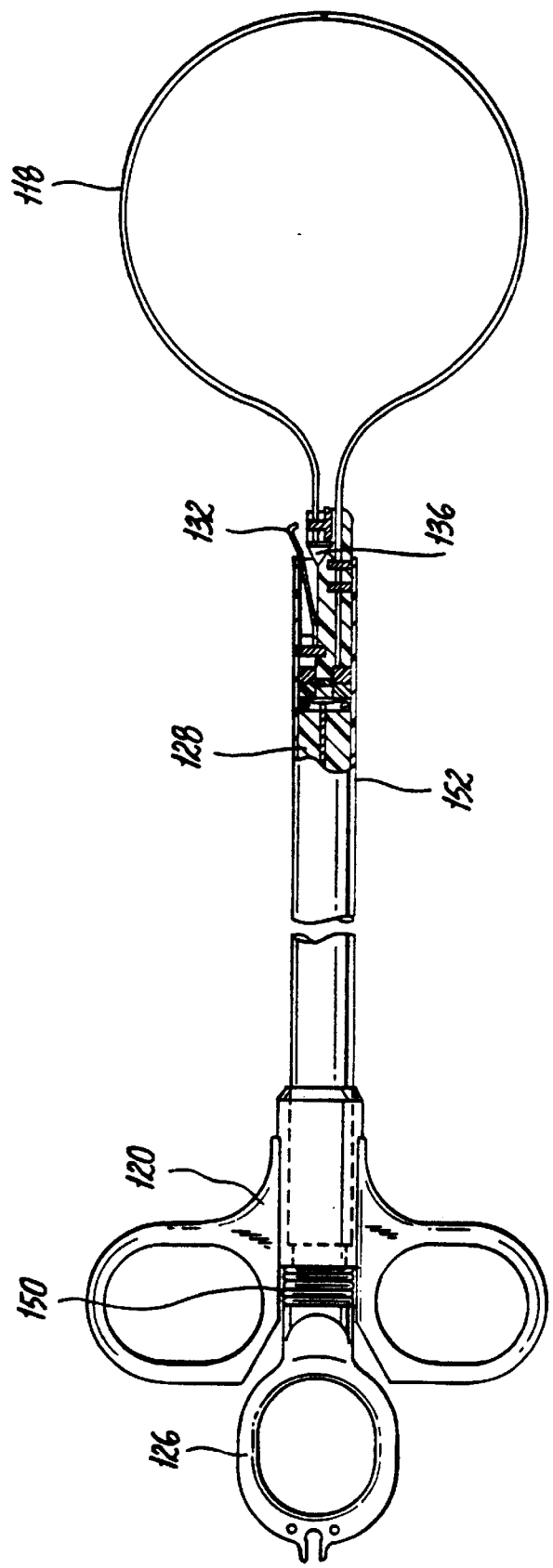
Figure 14:
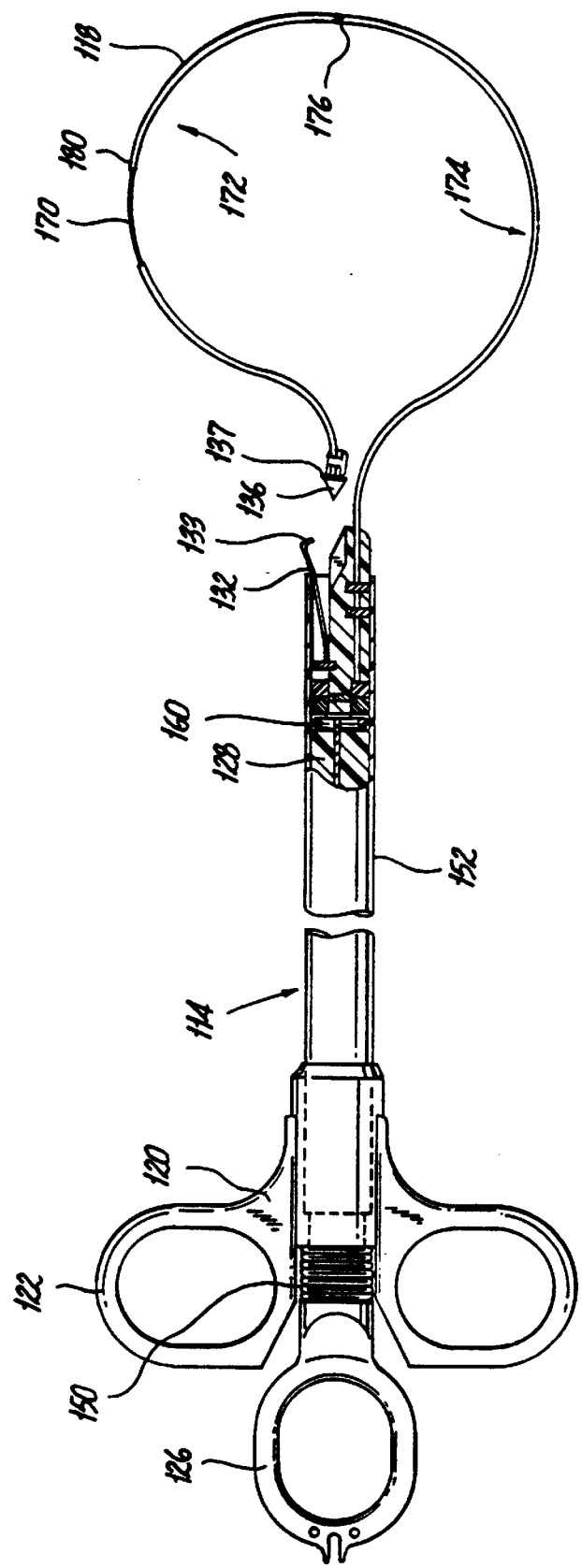

A preferred embodiment of detaching the grasping loop is shown in FIGS. 12–14. In FIG. 12, inner rod 128 is almost fully disposed in the distal most position, wherein the distal portion of connector mechanism 130 is positioned just inside the distal end of outer tube 152 and spring 150 is in contact with both actuator grasping ring 126 and body 120. In this position, connector mechanism 130 maintains loop 118 in a closed position. Connector mechanism 130 includes latch spring 132 pinned to inner rod 128 by pin 134 and bullet clip 136 secured to one end of loop 118 by pin 138. The other end of loop 118 is pinned to inner rod 128 by pins 140.

Turning to FIGS. 13 and 14, further distal movement of inner rod 128 compresses spring 150 and moves connector mechanism 130 at least partially past the distal end of outer tube 152. Spring 150 provides the surgeon with tactile feedback to indicate that the connector mechanism is in the attach/detach mode. In this mode/position, latch spring 132 is permitted to bias away from the longitudinal axis of center rod 128 and is in a position to either receive or release bullet clip 136. Hook 133 at the distal end of latch spring 132 is designed to grasp distal edge 137 of bullet clip 136. Through manipulation of the free end of loop 118, the surgeon can now attach or detach the loop.

With reference to FIG. 14, loop member 118 is shown with a preferred construction, metal band 170 covered with plastic 180. Loop member 118 is also preferably constructed in two portions, 172 and 174, which facilitate collapsation of the loop when withdrawn into outer tube 152 (see FIG. 11). Plastic 176 at the juncture of loop portions 172 and 174 provides for hinging action upon deployment and/or retraction of loop 118. Also shown in FIG. 14 is O-ring seal 160 to inhibit the flow of insufflation gas through the instrument. Additional O-ring seals or other sealing mechanisms can also be used. As set forth in the claims, "keyway connection means" refers to keyway connection 34, which includes dove-tail connectors 38 and 36, and equivalents thereof.

While the retractor device has been particularly shown and described with reference to the preferred embodiments, it will understood by those skilled in the art that various modifications and changes in form and detail may be made therein without departing from the scope and spirit of the novel features of the retractor device. For example, while specific mechanisms for attaching and detaching the loop member has been shown, any suitable structure allowing for attachment and detachment of the loop member can be used. Accordingly, modifications such as those suggested above, but not limited thereto, are to be considered within the scope of the present claims.

What is claimed is:

1. A retractor comprising:
    an elongated body portion;
    an actuator mechanism at least partially disposed at a proximal end of said body portion;
    a loop of material having first and second segments and being disposed at a distal end of said body portion, said loop of material being extendable and retractable with respect to said body portion in resconse to said actuator; and
    a coupling mechanism for separating said loop of material into said first and second at least two segments, said coupling mechanism including keyway connection means between said loop segments, for permitting reconnection of said first and second loop of material.

2. A retractor according to claim 1, further comprising a handle member for gripping said retractor, said actuator mechanism being disposed at least partially in said handle member.

3. A retractor according to claim 2, wherein said actuator mechanism includes a rotatable knob disposed on said handle member, said knob being operatively connected to a drive screw member disposed in said handle member for extending and retracting said loop of material from said body portion.

4. A retractor according to claim 1, wherein said body portion includes an outer tube member and an inner rod member slidably disposed therein, said loop of material being at least partially disposed on a distal end of said inner rod member and movable with said inner rod member in response to said actuator mechanism.

5. A retractor according to claim 3, wherein said actuator mechanism includes a rotatable knob being operatively connected to said inner rod member to extend and retract said loop of material from said body portion.

6. An endoscopic instrument comprising:
   a handle portion having an actuator mechanism at partially disposed therein;
   an elongated body portion extending from said handle portion, said body portion including an inner member slidable within an outer tubular member; and
   a grasping mechanism disposed at a distal end of said inner member remote from said handle portion, said grasping mechanism formed from a loop of material havina first and second ends, said first loop end being fixedly secured to the distal end of said inner member and the second loop end being detachably secured to the distal end of said inner member;
   wherein said grasping mechanism is movable between an retracted position in which said loop is substantially disposed within said outer tubular member, and an extended position in which said loop extends substantially outside said tubular member, said second end of said loop being detachable from the distal end of said inner member when said grasping mechanism is in said extended position.

7. An endoscopic instrument according to claim 6, further comprising a spring member disposed at the distal end of said inner member and attaching structure disposed at said loop second end adapted to be releasably engaged by said spring member.

8. An endoscopic instrument according to claim 6, wherein said inner member is slidable within said outer tubular member in response to movement of said actuator mechanism.

9. An endoscopic instrument according to claim 8, wherein said actuator mechanism comprises a rotatable knob member disposed on said handle portion, said inner member being coupled to said knob member through a drive screw assembly disposed in said handle portion.

10. An instrument comprising:
   a tubular body portion;
   an actuator mechanism at least partially disposed at a proximal end of the tubular body portion, the actuator mechanism including an inner rod member having proximal and distal end portions;
   an elongate endoscopic portion extending distally from the tubular body portion, the inner rod member being longitudinally slidable within the elongate endosocpic portion;
   a grasping loop having first and second ends, said first end being fixedly secured to the distal end of the inner rod member; and
   a connector mechanism at least partially associated with the distal end of the inner rod member, the connector mechanism including a clip secured to the second end of the grasping loop and a spring secured to the distal end of the inner rod member, the spring being adapted to releasably engage and retain the clip;
   wherein said grasping loop is movable in response to said actuator mechanism from a first position, wherein at least a portion of the grasping loop is disposed within said body portion to a second position, wherein a portion of the grasping loop that was disposed within said body portion in said first position is disposed outside said body portion.

11. An endoscopic instrument according to claim 10, wherein the spring moves from a first position to a second position upon longitudinal movement of the inner rod member.

12. An endoscopic instrument according to claim 7, wherein said spring member has proximal and distal end portions and said spring proximal end portion is fixedly secured to the distal end of said inner member and the spring distal end portion is free to releasably engage the attaching structure disposed at said loop second end.

13. An endoscopic instrument according to claim 12, wherein the attaching structure is a bullet-shaped clip.

\* \* \* \* \*